United States Patent [19]

Fitz-James

[11] Patent Number: 4,609,550

[45] Date of Patent: Sep. 2, 1986

[54] BACILLUS CEREUS SUBSPECIES ISRAELENSIS

[75] Inventor: Philip C. Fitz-James, London, Canada

[73] Assignee: The University of Western Ontario, Health Sciences Centre, London, Canada

[21] Appl. No.: 459,596

[22] Filed: Jan. 20, 1983

[30] Foreign Application Priority Data

Jul. 9, 1982 [CA] Canada ................................ 407032

[51] Int. Cl.<sup>4</sup> ..................... C12N 1/06; C12N 15/00; C12N 3/00; C12N 1/20; C12R 1/085; A01C 1/00; A01N 63/00

[52] U.S. Cl. ................................. 424/93; 435/242; 435/253; 435/172.1; 435/259; 435/261; 435/834; 47/58

[58] Field of Search .................. 424/93, 195; 435/242, 435/253, 261, 88, 832, 172.1, 259

[56] References Cited

U.S. PATENT DOCUMENTS

| | | | |
|---|---|---|---|
| 1,929,085 | 10/1933 | Suehs ...................................... | 99/11 |
| 2,908,614 | 10/1959 | Harrow ................................... | 167/78 |
| 3,271,243 | 9/1966 | Cords et al. ............................ | 424/93 |
| 3,651,215 | 3/1972 | Ibuki ....................................... | 424/93 |
| 3,702,359 | 11/1972 | Dulmage ................................ | 424/93 |
| 3,911,110 | 10/1975 | Smirnoff ................................. | 424/93 |
| 3,937,813 | 2/1976 | Clark ....................................... | 424/93 |
| 3,944,664 | 3/1976 | Kitagaki et al. ....................... | 424/93 |
| 3,946,107 | 3/1976 | Westall ................................... | 424/93 |
| 4,000,258 | 12/1976 | Shieh ....................................... | 424/93 |
| 4,107,294 | 8/1978 | Chauthani ............................. | 424/93 |
| 4,166,112 | 8/1979 | Goldberg ............................... | 424/93 |
| 4,187,290 | 2/1980 | Goldberg ............................... | 424/93 |
| 4,265,880 | 5/1981 | Spence ................................... | 424/93 |
| 4,277,564 | 7/1981 | Johnson ................................. | 435/242 |
| 4,450,236 | 5/1984 | Dean et al. ............................. | 435/253 |

FOREIGN PATENT DOCUMENTS

| | | | |
|---|---|---|---|
| 879078 | 8/1971 | Canada ................................... | 435/242 |
| 687428 | 5/1974 | Canada ................................... | 435/242 |
| 698579 | 5/1974 | Canada ................................... | 435/242 |
| 958330 | 11/1974 | Canada ................................... | 435/242 |
| 1071100 | 5/1980 | Canada ................................... | 435/242 |

OTHER PUBLICATIONS

Tyrell, Dana J., *Chemical Abstracts*, v. 94, 115975e, "Comparative Biochemistry of Entomocidal Parasporal Crystals . . . ".

Fitz-James, 7th Annual Ontario Mosquito Control Association Meeting, Mar. 1-2, 1982.

Fitz-James, Report to the Ministry of the Environment, Jan. 1982.

Y. Wakisaka et al.: "Asporogenous *Bacillus thuringiensis* Mutant Producing High Yields of Delta-Endotoxin", *Applied and Environmental Microbiology*", vol. 43, No. 6, Jun. 1982, pp. 1498-1500.

J. Nishiitsutsuji-uwo et al.: "Sporeless Mutants of *Bacillus thuringiensis*", *Journal of Invertebrate Pathology*, vol. 25, 1975, pp. 355-361.

E. W. Davison et al.: "Comparative Field Trials of *Bacillus sphaericus* Strain 1593 and *B. thuringiensis* Var. *israelensis* Commercial Powder Formulations", *Journal of Economic Entomology*, vol. 74, No. 3, Jun. 1981, pp. 350-354.

*Chemical Abstracts*, vol. 96, No. 17, Apr. 26, 1982, p. 315, No. 137948s, Columbus, Ohio, USA; J. F. Charles et al.; "Histopathology of *Bacillus thuringiensis* var. *israelensis* Delta-Endotoxin on *Aedes aegypti* Larvae [Dip.:Culicidae], & Entomophaga, " 1981, 26(2), 203-212.

P. C. Fitz-James: "Spore Formation in Wild and Mutant Strains of *B. cereus* and Some Effects of Inhibitors", Colloque CNRS, Center Nationale Researche Scientific, 1963, published in 1965.

*Primary Examiner*—Thomas G. Wiseman
*Assistant Examiner*—Robin Lyn Teskin
*Attorney, Agent, or Firm*—Brumbaugh, Graves, Donohue & Raymond

[57] ABSTRACT

Biologically pure mutants of *Bacillus cereus* subspecies *israelensis* (also called *Bacillus thuringiensis* sub. sp. *israelensis*) which are substantially non-spore-forming but which are capable of forming inclusion bodies toxic to Diptera larvae are described. A spore-free insecticide based on these inclusion bodies as well as the method of producing same are disclosed.

19 Claims, 9 Drawing Figures

BACILLUS CEREUS SUBSPECIES ISRAELENSIS

This invention relates to a substantially non-spore-forming mutant of *Bacillus cereus* subspecies *israelensis*, an insecticide for controlling insects of the order Diptera in the larval stage and a process of preparing the insecticide.

It is known that various strains of *Bacillus cereus* produce inclusions which are or which carry substances toxic to the larval stage of certain insects such as insects of the order *Lepidoptera, Diptera* and others. Subspecies *thuringiensis* was found to form inclusion bodies which carry substances toxic to larvae of Lepidopterans and subspecies *israelensis* was found to form inclusion bodies which carry substances toxic to larvae of dipterans. The latter species was first described in a publication by H. de Barjac in CR Acad. Sci., Paris, 286, 797–800 and 1175–1178, Serie D, 1978. At the time subspecies *thuringiensis* was thought to be a separate species and, as a result, subspecies *israelensis* was thought to be a subspecies of *Bacillus thuringiensis*. Even presently subspecies *israelensis* is often referred to as a subspecies of *Bacillus thuringiensis* or as BTI. However, in the following subspecies *israelensis* will be referred to as a subspecies of *Bacillus cereus* or as BCI.

The wild type of *Bacillus cereus* is a spore-forming organism. As in all bacilli sporulation is a seven stage process. In stage 1 the transition from a replicating cell to a stationary stage takes place. In stage 2 and early stage 3 development of the forespore takes place. In late stage 3 the cell becomes "committed" to proceed with the formation of a spore. In stage 4 the cortex is developed. In stage 5 coat protein is deposited. In stage 6 dehydration of the spore protoplast and accumulation of dipicolinic acid and calcium in the spore takes place. In stage 7 a lytic enzyme causes lysis of the cell and release of the spore.

The critical stage for the formation of the inclusion body usually appears to be stage 2 of the sporulation. For example, in *Bacillus cereus* subspecies *medusa* inclusion formation begins against the cell membrane before the start of sporulation in late vegetative growth. Typical inclusions grow and differentiate with the spore. In *Bacillus cereus* subspecies *thuringiensis* and its many variants which are toxic to Lepidoptera larvae the inclusion is initially formed against the face of the stage 2 forespore. In *Bacillus cereus* subspecies *israelensis* the inclusion formation appears to start either before or with stage 2. If the formation starts before stage 2 the inclusion is deposited at a membrane site somewhat remote from the site of spore formation. If the inclusion formation starts in stage 2, the inclusion is deposited against the membrane adjacent to the developing spore. In a few cells, membrane deposition of inclusion protein has been observed at both sites. In subspecies *israelensis* the inclusion grows throughout stages 3 to 6 into a multicrystalline inclusion eventually covered by a thin "skin". This skin generally has many small regular virus-like particles layered on the outside of the inclusion. These particles are apparently some kind of defective ribonucleic acid containing phages which also exist in free form and which are induced by stage 2 of the sporulation independent of the synthesis of protein contained in the inclusion. Structures substantially identical to the phage are also found on and adjacent to the inclusions of subspecies *medusa* (see G. S. Hendry, J. B. Gillespie and P. C. Fitz-James, J. Virol. 18, 1051–1062, 1976), but are not found in any of the subspecies *thuringiensis* which are toxic to *Lepidoptera* larvae.

Thin section micrographs of ripe inclusions show both light and dark stained crystalline structures enclosed in a thin skin. Preliminary evidence indicates that the lighter stained crystals are the sites of the toxin. Physical fixation by freezing and metal shadowing of exposed samples also show the multicrystalline nature of the inclusion of subspecies *israelensis*.

Centrifugation of spores and the inclusions of subspecies *israelensis* in a gradient of sucrose or diatrizoate show the toxin to be entirely localized in the inclusions. The spores are non-toxic. Paralysis of test larvae can be achieved by as few as $10^4$ inclusions/ml. A typical *Bacillus cereus* spore is characterized by coat layers which are distinct in molecular array with those on spores of other soil spore-forming bacilli. The coat structure and, in many cases, the coat polypeptide separable by polyacrylamide gel electrophoresis are identical on the spores of *Bacillus cereus* and on the spores of those subspecies which form parasporal inclusions toxic to *Lepidoptera* or *Diptera* larvae. Accordingly, it is generally not possible by structural and biochemical procedures to distinguish *Bacillus cereus* itself from subspecies such as *israelensis, thuringiensis, medusa* and its many relatives. Furthermore, it is not generally possible to distinguish on a structural basis the spores of the above-mentioned subspecies and those of subspecies *anthracis* which is also a toxigenic species of *Bacillus cereus* and which causes anthrax.

The specific properties of various subspecies of *Bacillus cereus* as compared to a standard *Bacillus cereus* appears to be due to plasmids or extrachromosomal bits of desoxyribonucleic acid. It has been found that "curing" of a number of these subspecies leads to the formation of a *Bacillus cereus*, also called Cry (-) *Bacillus thuringiensis*, which lacks a plasmid component present in the wild type and, in cases where the formation of a toxic inclusion body is associated with the lacking plasmid, the cured subspecies is devoid of toxicity. For example, Knudsen et al reported that when subspecies *anthracis* is cured such as by growing the culture at or above 42° C. plasmid loss occurs, i.e. the so treated *anthracis* does no longer form the toxin (C. B. Knudsen, B. Ivins and P. Mikesell, Abstract H29 ASM Annual Meeting 1982). Work by the present inventor and others has shown that the same is true for several other subspecies such as *israelensis, thuringiensis* and *medusa*. When these subspecies are grown at or above 42° C. plasmid loss occurs and the resulting culture does no longer form the respective specific inclusion bodies.

An apparent plasmid uptake has been reported by Toumanoff who found induction of inclusion formation and toxicity to Lepidoptera larvae in a culture of non-toxic type of *Bacillus cereus* which was repeatedly passed through the gut of wax moth larvae (C. Toumanoff, Ann. Inst. Pasteur Paris, 90, 1, 1959). Thus, even though the precise mechanism of interchangeability is not known it appears that subspecies of *Bacillus cereus* can, under certain conditions, lose their specific toxigenic characteristics, and it appears possible that, under certain conditions, *Bacillus cereus* can develop toxigenic characteristics to become one of its subspecies.

The use of inclusion bodies from *Bacillus cereus* subspecies *israelensis* as insecticide active against *Diptera* larvae is known (H. de Barjac, CR Acad. Sci., Paris, 286, 797–800 and 1175–1178, 1978). The diptericidal crystalline protein contained in inclusion bodies of subspecies *israelensis* has been shown to have a different polyacrylamide gel electrophoresis pattern from the protein in inclusion bodies of subspecies which are not toxic to *Diptera* larvae (H. E. Huber, P. Luthy, H.-R. Ebersold and J.-L. Cordier, Arch. Microbiol 129, 14–18, 1981).

The article of Huber et al as well as other literature references mentioned in this specification are incorporated by reference.

The toxic effect of the inclusion bodies of subspecies *israelensis* is quite host specific and causes paralysis and intestinal disorder in the host. Such preparation containing the inclusion bodies are derived from the wild type of *Bacillus cereus* subspecies *israelensis* which forms spores. Since in the wild type the inclusion bodies are released simultaneously with the spore in stage 7 of sporulation, and since it is relatively difficult to separate the inclusion bodies from the spores, these preparations contain besides the toxic inclusion bodies a great number of viable spores. One of such preparation is described in U.S. Pat. No. 4,166,112 to Goldberg.

When such spore-containing preparations are used for the control of insect larvae, these viable spores may proliferate and thus, spread uncontrolled. At present it is not known whether deposit of great quantities of *Bacillus cereus* subspecies *israelensis* in the form of viable spores will (a) upset the soil balance of aerobic bacilli, (b) encourage emergence of the related subspecies *anthracis* so as to cause an increase in the occurrence of anthrax, or (c) have other potentially damaging effects. Under certain conditions interchange of plasmids can occur between vegetative cells of two different subspecies of *Bacillus cereus*. (Gonzalez et al. 1982. Proc. Nat. Acad. Sci. USA (in press) and, Gonzalez J. M. and B. C. Carleton 1982 in Genetic Exchange, Streips, Guild, Gordal and Wilson eds. pp. 85–95. Marcel Dekker N. Y.

To avoid such potentially adverse effects of the spores it has been proposed to chemically treat the spores to render them non-viable such as described in Canadian Pat. No. 958,330 to Utsumi et al for a preparation which is active against Lepidoptera. In such a chemical treatment of the spore-containing insecticide, care has to be taken not to affect the insecticidal activity of the preparation at the same time.

In an effort to overcome the disadvantages of the prior art the present invention provides mutuants of *Bacillus cereus* subspecies *israelensis* which generally do not have spore-forming qualities but which retain the ability of forming inclusion bodies toxic to Diptera larvae. The mutants are obtained by screening wild type subspecies *israelensis*. The mutants release toxic inclusion bodies into the culture medium which can easily be separated and applied for the control of *Diptera* larvae such as mosquito and black fly larvae. The inclusion bodies are also active against larvae of the midgefly.

Accordingly, in one aspect of the present invention there is provided a biologically pure mutant of *Bacillus cereus* subspecies *israelensis* which is substantially non-spore-forming, while being capable of forming inclusion bodies toxic to insects of the order Diptera in the larval stage, and which is selected from the group consisting of mutants bearing deposit numbers 1178, 1179 and 1180 with the culture collection of the University of Western Ontario, London, Ontario, Canada.

In a second aspect of the invention there is provided a method for producing a substantially spore-free insecticide active against insects of the order Diptera in the larval stage comprising growing a biologically pure non-spore-forming mutant of *Bacillus cereus* susbspecies *israelensis* in a culture medium to the stage of formation of toxic inclusion bodies and lysis of the cells, and separating the toxic inclusion bodies from the culture medium.

In a further aspect of the present invention there is provided an insecticide active against insects of the order Diptera in the larval stage comprising as an active ingredient an effective larva killing concentration of substantially spore-free toxic inclusion bodies.

In yet a further aspect of the invention there is provided a method of controlling insects of the order Diptera in the larval stage comprising applying to larval habitats an effective concentration of substantially spore-free toxic inclusion bodies.

In an effort to arrive at a mutant of *Bacillus cereus* subspecies *israelensis* which does not form spores, the wild type of this subspecies was subjected to several stimuli such as exposure to ultraviolet, freeze-drying, growth on partly dehydrated agar, growth at 43° C., and growth in the presence of a mutagen. Grey or lytic colony segments or colonies showing a decreased whiteness on sporulation were picked and replated. Vegetative cell mobility of both the wild type and the mutant made pure cultivation of a mutant showing initial promise on phase-contrast light microscopy difficult.

Mutants CB3-90 and CB3-91 according to the invention were isolated in the following way. An exponentially growing culture of the wild type of subspecies *israelensis* in fluid medium was treated with the mutagen N-methyl-N'-nitro-N-nitrosoguanidine. After aeration of the culture in the mutagen the cells were washed, resuspended in nutrient broth and plated onto sporulation medium. After incubation colonies of decreased whiteness were picked and examined by phase-contrast microscopy. This lead to the finding of the two mutants CB3-90 and CB3-91 which, after somewhat prolonged growth on agar, form inclusions but no spores. Thus, when the cells lyse no spores are released into the culture medium. As in the wild type the inclusion bodies contain crystalline protein toxic to *Diptera* larvae. In mutant CB3-90 the sporulation process appears to be blocked at early stage 3, whereas in mutant CB3-91 the sporulation process appears to be blocked at late stage 2. Accordingly, CB3-90 may be referred to as Spo III mutant and CB3-91 a Spo II mutant. Both are relatively slow lysing stable mutants, apparently having more stable cell walls than the wild type. As a result the inclusion bodies are not readily released into the culture medium, but tend to remain enclosed by the cell wall for a prolonged period. In cultures which are allowed to grow for less than about 24 hours generally less than 20% of the inclusion bodies are to be found in the culture medium. With prolonged growth a higher percentage of the inclusions are released. No viable spores were recovered from cultures of these two mutants and no reversion of the mutants to the wild type was observed.

Mutant group CB3-100 to 104, type strained through to a stable mutant now called CB3-104R, was isolated from a series of platings of wild type subspecies *israelensis* which had been subjected to freeze drying. This group appeared to originate from a single colony. The 5 mutants varied primarily in their rate of reversion to the wild type. All have low reversion rates, with CB3-104R having the lowest reversion rate. When cultured to avoid repeated over-aging of the culture, CB3-104R has a reversion rate of less than 1 in $10^8$. In this mutant the sporulation process appears to be blocked at late stage 2 or early stage 3.

Colonies of CB3-104R which are 18 to 24 hours old are less white than colonies of the wild type and become greyish with inclusion ripening. With continued incubation beyond 24 hours the lysing colonies send out repeated rings of renewed growth giving the ripe colonies a ridged appearance when viewed in indirect light. The formation of inclusions is rapid and the cells have an active lytic system. Contrary to the slow lysing mutants CB3-90 and CB3-91 lysis of the CB3-104R cells results in the mass release of inclusion bodies and some cell debris into the culture medium, but does not result in the release of any spores. Almost every cell in the culture forms a set of toxic inclusions following overnight growth. As reversion to the wild type is associated with secondary growth, it can substantially be avoided by avoiding secondary growth in older colonies. This can be effected by selecting a relatively young area of the colony and growing it for inoculation and by allowing the inoculated culture batch to proceed rapidly, preferably within about 18 to 20 hours, through one growth cycle to completion of growth, through the stationary phase, through the post stationary synthesis of toxic inclusion bodies to their release upon lysis of the cells. Growing of the culture in a medium containing a minimal amount of nutrients and, preferably, little or no sugar, also enhances rapid growth through one growth cycle to lysis due to relatively early depletion of the medium by the culture.

The mutants CB3-90, CB3-91 and CB3-104R have been deposited on June 22, 1982 with the culture collection of the University of Western Ontario, London, Ontario, Canada, and have been granted deposit numbers 1178, 1179 and 1180, respectively. This culture collection is listed as No. 262 by the Canadian Committee on Culture Collections of Micro-organisms (National Research Council of Canada, Ottawa, Canada) and as No. 80 by the World Federation of Culture Collections of the International Association of Microbiological Societies (c/o S. M. Martin, Division of Biological Sciences, National Research Council of Canada, Ottawa, Canada, or V. B. D. Skerman, Department of Microbiology, University of Queensland, Brisbane, Australia).

Mutant CB3-104R has also been deposited on July 2, 1982 with the American Type Culture Collection, Rockville, Md., U.S.A. and has been granted deposit number ATCC 39,152.

Like their parent strain *Bacillus cereus* subspecies *israelensis* the mutants according to the invention are gram-positive bacteria. The mutants grow well on common sporulation media. It appears that the richer the medium is in nitrogen, mainly peptones, the higher the yield of inclusion protein.

In cultures of these non-spore-forming mutants the entire energy of the growing cells is directed to the formation of toxic inclusion bodies. Accordingly, the mutants produce the toxic inclusion bodies more efficiently than the wild type which forms spores as well as inclusions. As mentioned previously, the inclusion bodies of subspecies *israelensis* may be deposited against at least two different membrane sites. In the wild type of subspecies *israelensis* formation of two inclusion bodies in one cell occurs relatively rarely, whereas in the mutants according to the invention, most particularly in CB3-104R, multiple inclusion protein deposition is considerably more prevalent. The toxicity of the inclusion bodies of the wild type *israelensis* and of those of the mutants is identical. The mutants, however, can produce about 1.5 times more toxin than the wild type.

Once the mutant cultures have been grown to lysis, generally within about 18 to 20 hours at about 30° C., the inclusion bodies are separated from the culture medium such as by centrifugation, filtration or the like. If, as may be the case for mutants CB3-90 and CB3-91, more than 10 to 20 percent of the inclusions are cell wall enclosed, these may be liberated by rupturing of the cells by any microbiologically accepted means. For example, the pellet may be subjected to relatively high shearing stress such as by application of ultrasound, by passing the pellet through a French Pressure cell under pressures of 10-20,000 psi. etc. Such treatment breaks up any clumps and any remaining intact vegetative cells. The latter may also be achieved by drying at low temperatures 30°-40° C. which kills such remaining cells without affecting the inclusion bodies.

Generally, however, particularly in the case of the CB3-104R mutant, which on lysis releases the inclusion bodies into the culture medium separation of the inclusion bodies from the culture medium can be effected by merely subjecting the culture to centrifugation or filtration. The resulting pellet is suspended in an antiflocculant medium and is ready for industrial formulation. Dilution of the product with any of the commonly used diluents and fillers such as diatomaceous earth or the like may then be effected. Any intact vegetative cells which may be contained in the pellet should not present any danger when spread together with the inclusion bodies, since these cells have very little resistance to heat, dehydration, etc. Alternatively, such intact cells may be ruptured or otherwise inactivated by any convenient means as long as the activity of the inclusion bodies is not affected.

A convenient procedure has been developed for suspending the products of fermentation of *Bacillus (cereus) thuringiensis* sub sp *israelensis* #CB3-104R. To avoid the clumping which otherwise tends to occur, we shake the crude pellet in a water solution of "Tween 20" (trade mark) (Atlas Powder Co. Ltd.) 0.02%. Aggregation is inhibited. To prevent contamination sodium azide can be added to a final concentration of 0.04%. Neither the Tween 20 or azide affect the toxicity to mosquito larvae.

Toxicity studies in both laboratory basins and natural ponds performed with various mosquito larvae and with toxin levels in the basins and ponds of at least $10^4$ inclusions/ml show a rapid decline in the number of larvae. Generally the larvae were paralyzed within 20 to 90 minutes after application of the toxin at the above levels. Lower toxin concentrations may be used if rapid paralysis is not required. The toxin may be applied directly to the basin or pond or may be applied in a slow-releasing form such as by way of floats which contain toxin embedded in Plaster of Paris.

In laboratory basins the toxicity to larvae can persist for weeks and even several months. In natural ponds, however, practically no residual toxin can be found after a relatively short time, such as 3 to 4 days. That means that the natural ponds are able to support the development of any surviving or freshly hatched larvae within a few days of the administration of the toxin. This is thought to reflect a high content of active proteases in pools which are rich in organic material. Such proteases would inactivate the toxin. It follows that in field applications repeated toxin application may be necessary for mosquito species such as *Culex*, while one toxin application during the larval development period may be sufficient for species with a limited life cycle such as *Anaopheles*.

IN THE FIGURES.

FIGS. 1 and 2 show cells of the wild type in various stages of sporulation;

FIG. 3 shows spores and inclusion bodies after lysis of cells of the wild type;

FIG. 4 shows cells of mutant CB3-90 in various stages prior to lysis;

FIG. 5 shows lysed and lysing cells of mutant CB3-91;

FIG. 6 shows cells of mutant CB3-104R in the early stages of inclusion formation;

FIG. 7 shows lysed and lysing cells of mutant CB3-104R;

FIG. 8 shows inclusion bodies after complete lysis of CB3-104R cells; and

DISCOVERY OF MUTANTS CB3-90 AND CB3-91

A culture of the wild type (W.T.) of *Bacillus cereus* subspecies *israelensis* (BCl) was grown in either the solid or fluid form of a Grelet blood base medium (GBBM). The medium is a mixture of a salt component and blood base medium (BBM). The salt component contained per liter:

10 g $KNO_3$, 1.7 g $KH_2PO_4$, 1.7 g $K_2HPO_4$, $K_2SO_4$ 174 mg, 60 mg. $MgSO_4$, 2.2 mg $MnSO_4.H_2O$, 5 mg $Fe_2(SO_4)_3$, 14.4 mg $ZnSO_4.H_2O$ and 110.9 mg $CaCl_2$. The $CaCl_2$ was bottled separately in 10 ml of water and added to the other salts in 990 ml after autoclaving (Grelet, Ann. Inst. Pasteur Paris 81, 430, 1951). BBM; autoclaved separately, contained 0.5% proteose peptone #2, 0.5% proteose peptone #3, and 0.32% nutrient broth which are all Difco (Trademark) products.

The routine laboratory mix of this medium in fluid form or in 1.5% agar after sterilization was 65 ml of salt component plus 15 ml of BBM.

Figure 1:
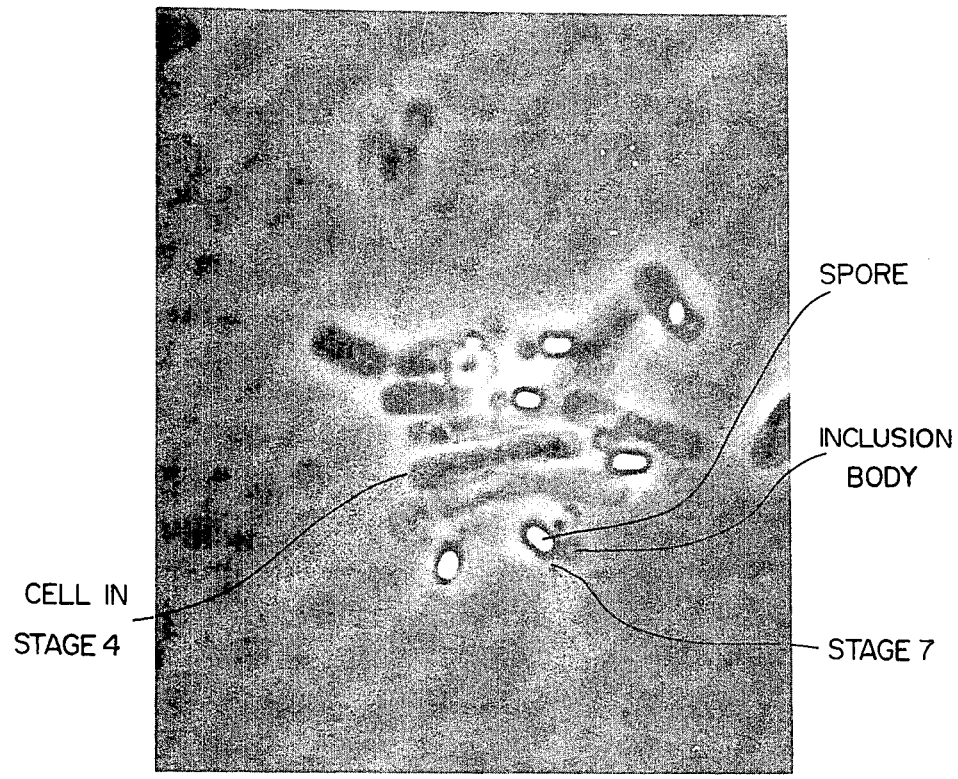
FIGS. 1 to 8 show phase-contrast light micrographs of cell colonies of the wild type and various mutants of *Bacillus cereus* subspecies *israelensis* in various stages of development about 4000 X magnified.
Figure 2:
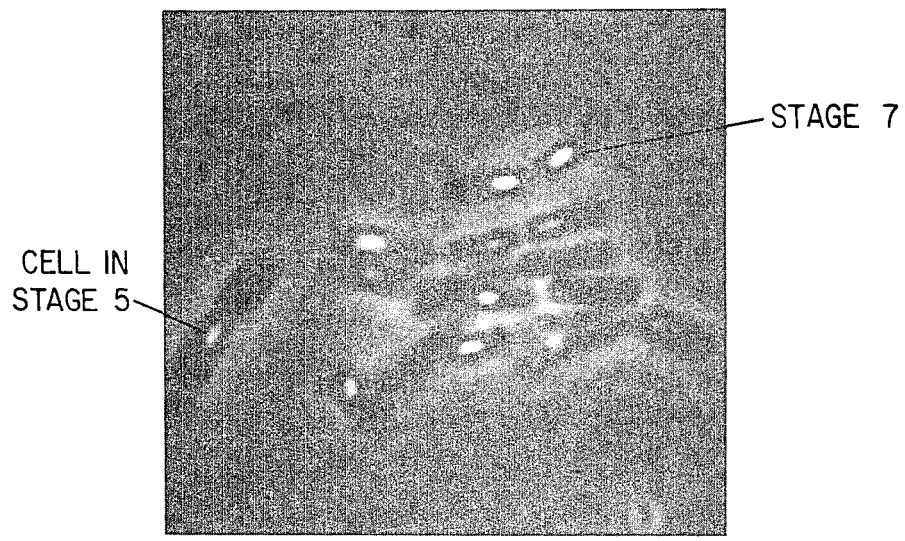
Figure 3:
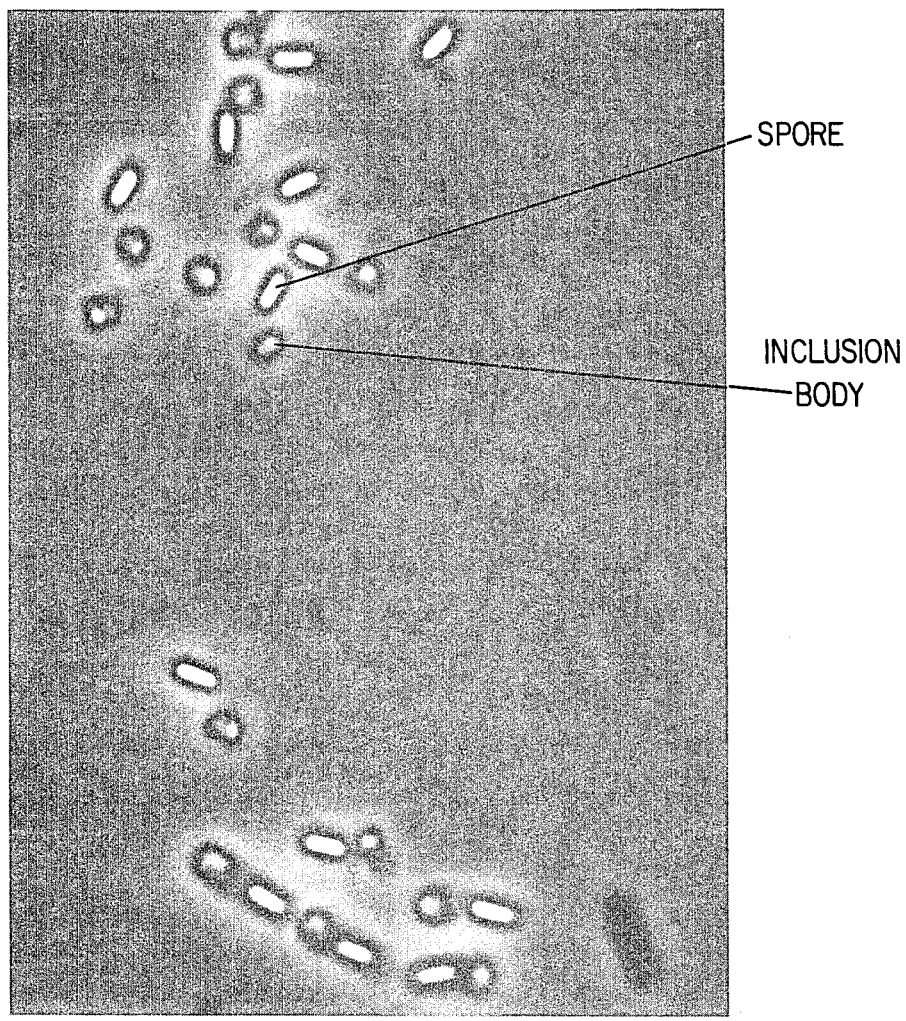
Figure 4:
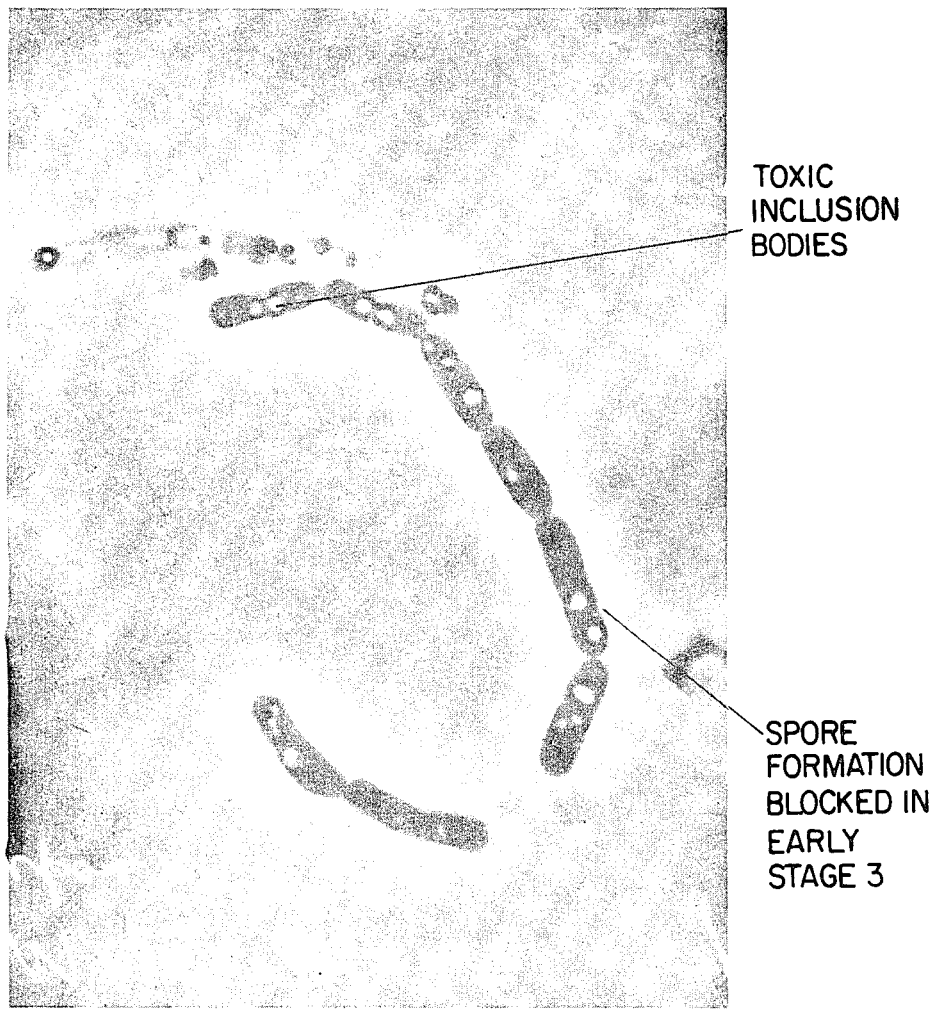

Once the culture reached exponential growth, it was treated with N-methyl-N'-nitro-N-nitrosoguanidine to a final concentration of 100 u g/ml. After 20 minutes aeration in the mutagen, the cells were washed, resuspended to 10 times their original concentration and 1 ml lots were added to 10 ml of nutrient broth, aerated overnight and then plated onto sporulation medium consisting of GBBM in agar form. After 24 hrs incubation at 30°-32° C. grey or lytic colony segments or colonies showing decreased whiteness were picked and replated. Mutant colonies had a characteristic granularity on preparing of cover glass smears for examination by phase-contrast microscopy. This led to the finding of two mutants, CB3-90 and CB3-91, which after somewhat prolonged growth and lysis on GBBM agar formed toxic inclusion bodies, one or more per cell (FIG. 4). No viable spores were recovered from cultures of these two mutants. The sole product of "sporulation" were inclusion bodies.

Figure 5:
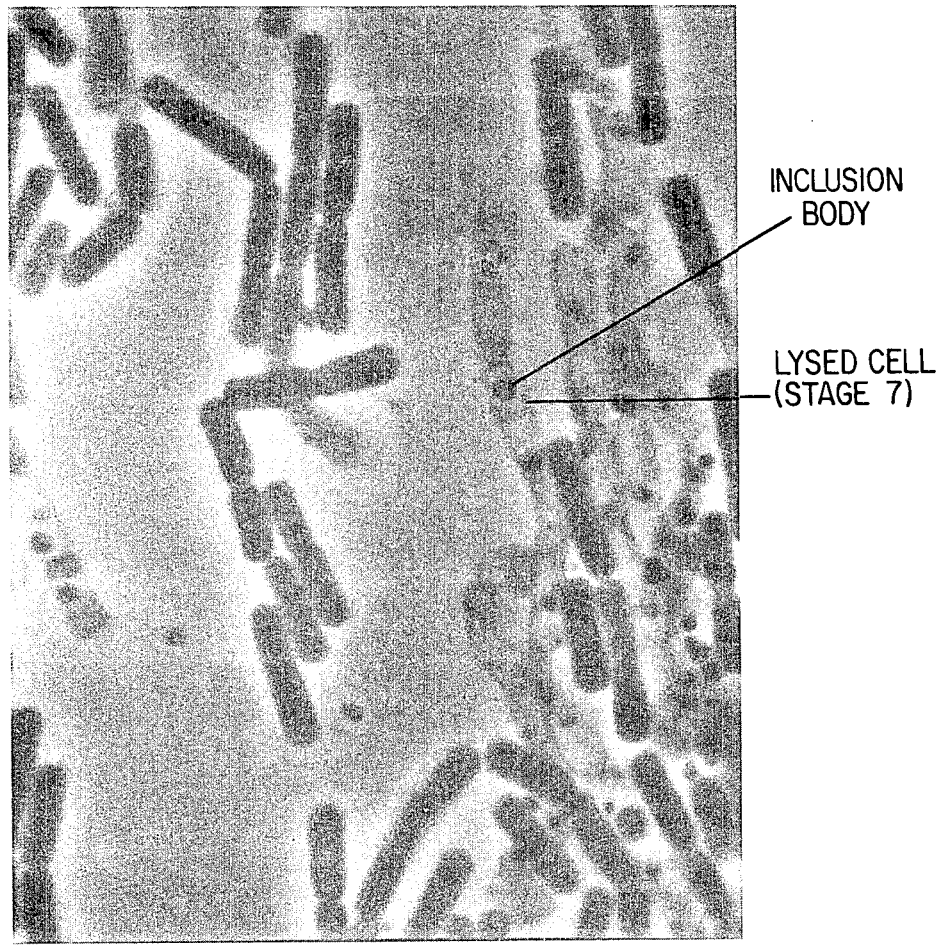

Light microscopy after 24 hrs of growth under the above conditions showed that only about 10% or less of the inclusion bodies had been released into the culture medium, the other 90% were cell wall enclosed (FIG. 5). After prolonged growth up to 48 h about 50% of inclusion bodies were released.

DISCOVERY OF MUTANTS CB3-104R

Figure 6:
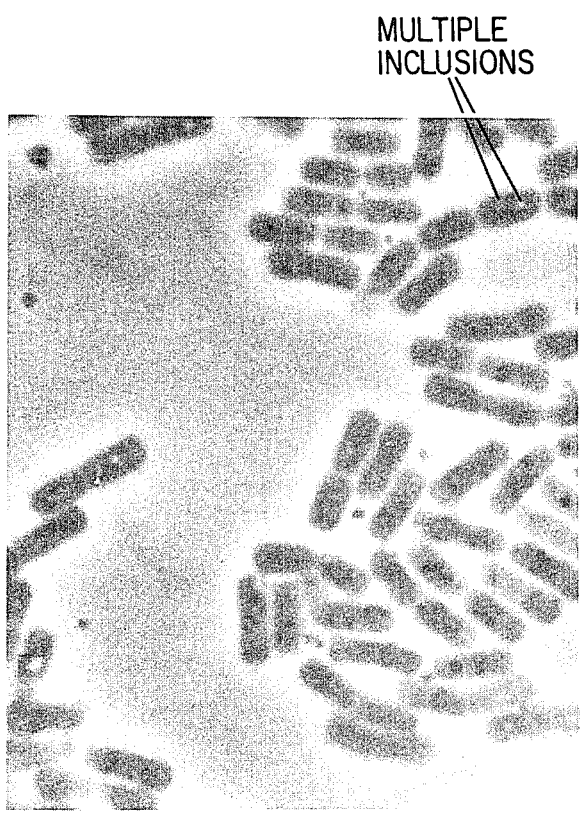
Figure 7:
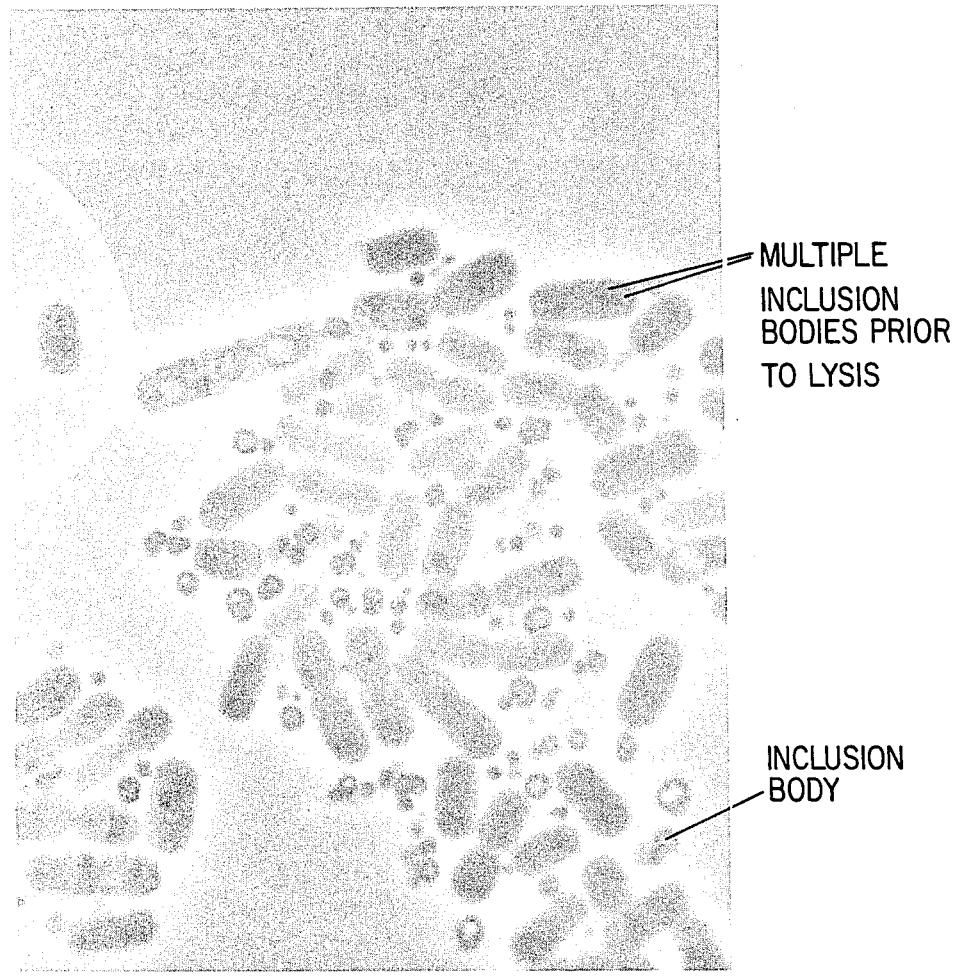

A culture of W.T. BCl was subjected to freeze drying. A series of 8 platings on 65:15 GBBM medium in agar form followed. Colonies showing decreased whiteness were picked and examined by phase-contrast microscopy. This led to the finding of mutant CB3-104R which had a reversion rate of less than $1/10^8$ when it was cultured to avoid repeated over-aging of the growth. The production of inclusions was robust and quick. Almost every cell in the culture formed a set of two toxic inclusions following overnight growth (FIGS. 6 and 7). By selecting a relatively young area of a colony for propagation of innocula and by allowing the main batch to proceed within 18 to 20 hrs to sporulation in relatively lean aerated fluid GBBM medium, a batch essentially free of revertants was obtained. CB3-104R grown in a 15 liter batch of 65:15 fluid GBBM medium yielded about 3 grams of toxic protein after 28 hrs of aeration followed by centrifugation. The culture was stored as a freeze dried pellet or by freezing a 6 to 8 hr growth in beef heart infusion broth from Difco with 10% glycerol.

Figure 8:
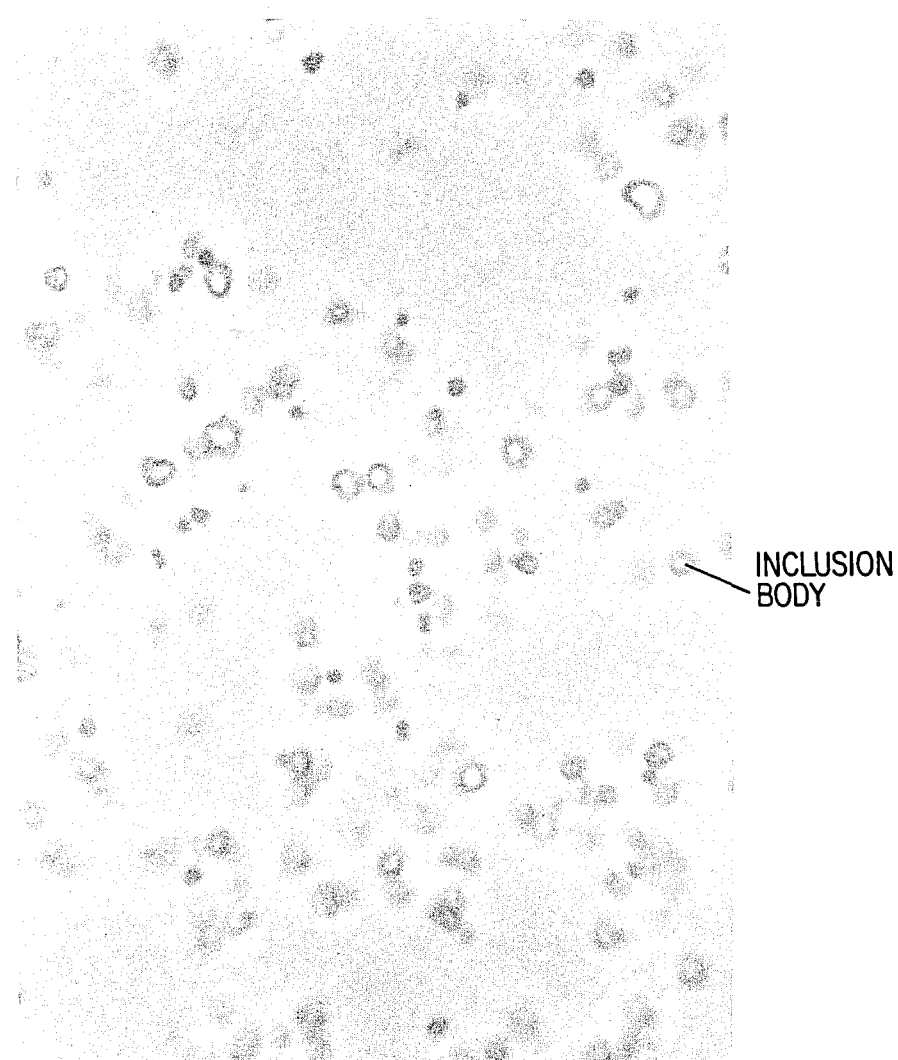
Figure 9:
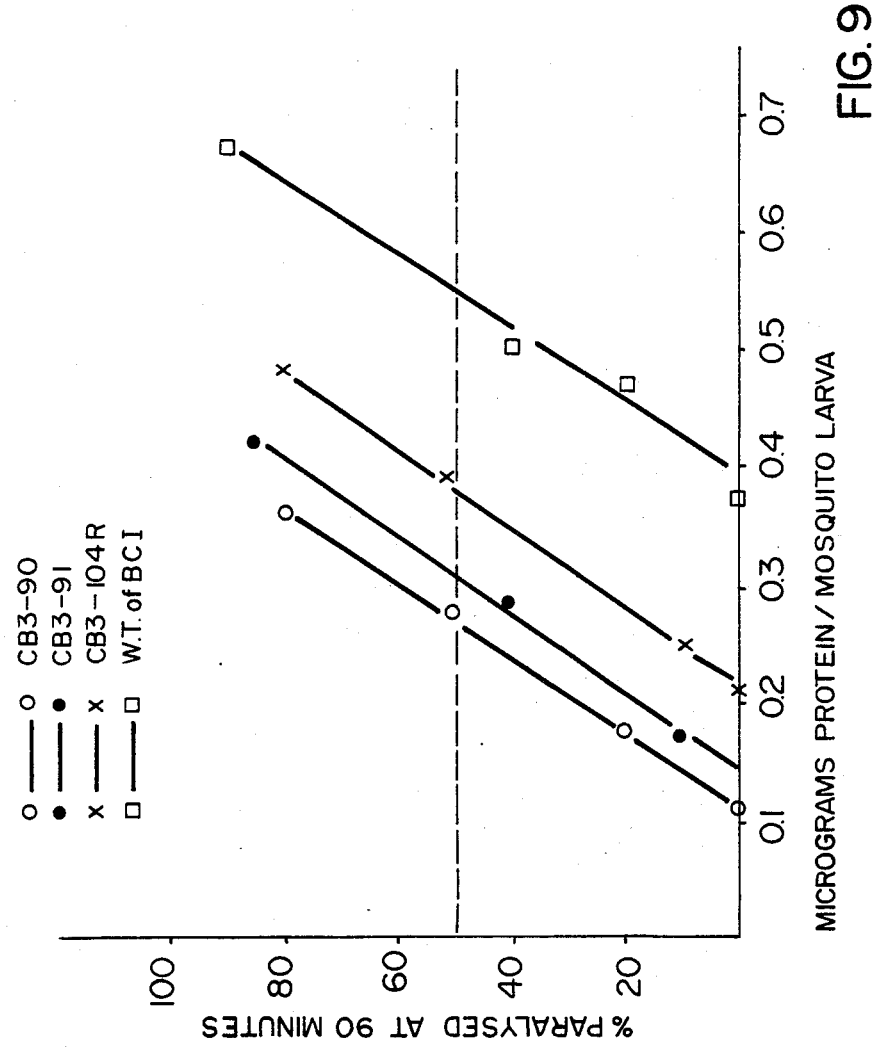
FIG. 9 illustrates the relationship between the amount of toxin administered and the extent of paralysis caused in the larvae.

On lysis practically all inclusion bodies were released into the medium (FIG. 8) and could be collected by centrifugation.

EXAMPLE 1

Influence of the culture medium on the protein yield

The mutants CB3-90, CB3-91 and CB3-104R as well as W.T. of BCl were grown in either solid or fluid form of GBBM. The salt component was mixed with the nitrogenous base BBM in various ratios and the mutants and W.T. were grown in the resulting media for 20 to 30 hours. The cultures were aerated by reciprocal shaking and harvested by centrifugation of the culture. Remaining cells were disrupted and the inclusions were dispersed by passing the pellets through a French Pressure cell. Protein was extracted from the pellets by dispersion in 0.5% sodium dodecylsulfate and 50 mM DTE at ph 10.3, precipitated by the addition of trichloroacetic acid until a concentration of 10% was reached. The precipitated protein was determined after redissolving in 0.2 M NaOH by the method of Hees, Lees and Derr, 1978 (Anal. Biochem. 85:295). The results are shown in Table I.

TABLE I

| Protein Yield (ug/ml) for Different Media Mixes | | | | | | |
|---|---|---|---|---|---|---|
| Medium (ml) Salts | BBM | Peptone Concentration (mg/ml) | Cultures | | | W.T. of BCl |
| | | | CB3-90 | CB3-91 | CB3-104 | |
| 75 | 5 | 0.83 | 17.5 | 13.5 | 21 | — |
| 70 | 10 | 1.66 | 26 | 18.5 | 25 | 73.5 |
| 65 | 15 | 2.49 | 28 | 29 | 39 | |
| 60 | 20 | 3.32 | 36 | 42 | 48 | 67.1 |
| 55 | 25 | 4.15 | 40 | 45 | 57 | — |

The results in Table I show that media richer in nitrogenous base produce slightly better yields of protein. However, cultures in such nitrogen rich media required longer times of aeration until the inclusion bodies were ripe and were released.

The higher protein yields in the wild type were due to contaminating spore proteins entracted along with the toxic inclusion.

EXAMPLE 2

Comparison of Inclusion Yields of Wild Type and Mutant Cultures

W.T. and mutants CB3-90 and CB3-104R of *Bacillus cereus* subspecies *israelensis* were grown separately in batches of various sizes in a 65:15 GBBM medium either in fluid form or on 15% agar. Depending on the size of the batches and the number of inoculations required the cultures were allowed to grow between about 24 and 48 hrs at 28° to 30° C. The number of inclusion bodies formed per volume was determined by phase-contrast microscopy and the protein yield was measured as described in Example 1. Prior to determination of protein in the W.T. cultures these cultures were subjected to separation in a Renographin (Trademark of Squibb) gradient so as to separate spore protein from inclusion protein. The cultures were then concentrated to the volume indicated in column 4 of Table II and again the number of inclusion bodies and the protein yield were determined.

The results are shown in Table II. From column 8 it can be seen that CB3-104R produces considerably more inclusions per ml or $cm^2$ of culture than the W.T.

TABLE III-continued

| Culture | PD50 range in μg protein/larva |
|---|---|
| W.T. BCI | 0.55-0.67 |

Since the proteins were determined on a centrifugal pellet of lysed or lysing culture and the toxicity was determined on the dispersed culture, any non-toxic protein contaminating the extract elevated the dosage. Table III shows no significant difference between the toxicities of the 3 mutants, but the mutants appear to be about two times more toxic than W.T. Correcting for contaminating non-toxic protein, the data in Table III as well as the data in Table I (see Example 1) indicate that mutant CB3-104R produces toxin 1.5 times more efficiently than the W.T.

FIG. 9 shows that with larger amounts of toxin the PD50 is reached in a shorter time under the above conditions, however, even high doses of toxin did not reduce the time within which PD50 was reached below 16 to 20 minutes. This appears to be the time required for a larva to ingest enough inclusions, to liberate the toxin, for the toxin to act on its target and for the changes leading to paralysis to occur.

B. Experiments with moderate doses of 0.4 μg larva of $C^{14}$ labelled inclusion protein indicate an uptake of protein measurable by 10 minutes and peaking by 20.

TABLE II

Inclusion Yields of Wild Type (W.T.) and Mutant Cultures (CB-3) Grown on Agar and Fluid Media

| Culture type | Medium 65:15 GBBM | Vol or Area | Concentrate volume ml | Yields/ml of Concentrate: Inclusions # × $10^9$ | Yields/ml of Concentrate: Protein mg | Yields/ml of Concentrate: Dry wt. mg | Yields/ml or $cm^2$ of culture: Inclusion # × $10^7$ | Yields/ml or $cm^2$ of culture: Protein ug | Protein/Inclusion μg × $10^{-6}$ |
|---|---|---|---|---|---|---|---|---|---|
| W.T. | Fluid | 1230 ml | 5* | 5 | 2.5 | — | 2.0/ml | 10 | 0.5 |
| W.T. | Agar | 2900 $cm^2$ | 6* | 8.5 | 5.7 | — | 1.7/$cm^2$ | 11.7/$cm^2$ | 0.45 |
| CB3-90 | Agar | 3150 $cm^2$ | 6 | 5.2 | 2.06 | | 1.0/$cm^2$ | 3.9/$cm^2$ | 0.2 |
| CB-3-104R | Fluid | 300 ml | 5 | 4.8 | 2.16 | 6.35 | 8.0/ml | 36/ml | 0.45 |
| CB-3-104R | Agar | 2160 $cm^2$ | 20 | 4.2 | 4.4 | 6.1 | 3.8/$cm^2$ | 40.7/$cm^2$ | 1.04 |
| CB 3-104R | Fluid | 15 liters | 150 | 37.5 | 7.56 | 20.1 | 37.5/ml | 75/ml | 0.2 |
| CB 3-90 | Fluid | 15 liters | 150 | — | 7.5 | — | — | 14.9/ml | |

*purified from "Renografin" gradient

Toxicity Studies

W.T. and mutants CB3-90, CB3-91 and CB3-104R were grown separately in 65:15 or 60:20 GBBM medium for 18 to 20 h at 30° C. Following this the cultures were centrifuged. If more than 10 to 20% of the inclusions are cell wall enclosed, as may be the case in the pellets of CB3-90 and CB3-91 cultures, these were liberated by two passages through a French Pressure cell at 14000 psi. The protein yield was determined and the pellets were suspended in 0.14 M NaCl to a concentration of about $2\times10^9$ inclusions/ml suspension.

A. To samples of 10 ml distilled water each containing 10 3rd instar larvae of *Aedes egypti* various amounts of inclusion protein were added. After 90 minutes exposure at room temperature the percentage of larvae paralyzed was calculated and the dose of inclusion protein required to paralyse half of the larvae (PD50) was determined. The results are shown in FIG. 9 and Table III.

TABLE III

| Culture | PD50 range in μg protein/larva |
|---|---|
| CB3-90 | 0.28-0.33 |
| CB3-91 | 0.30-0.40 |
| CB3-104R | 0.25-0.38 |

Counting of dissected larvae show that 80% or more of the radioactivity is held in the mid-gut region.

C. Pellets of mutant cultures were suspended to a concentration of $2\times10^9$ inclusions/ml and the suspension was added to laboratory basins having volumes of 7 to 30 liters and to natural ponds until final concentrations of $10^4$ to $10^5$ inclusions/ml were reached. Alternatively inclusions were embedded in Plaster of Paris blocks and these attached to styrofoam sheets and floated on the natural or laboratory basins which were infested with mosquito larvae. In all tests not interfered with by rain fall the mosquito populations fell from 20-50 larvae/350 ml dipper to zero larvae in 24 hours. The direct addition of inclusions resulted in more rapid paralysis of the larvae than the slow release from Plaster of Paris floats, but the latter were more effective in long term studies in laboratory basins fed with yeast powder and ground-up purina chow. After 3-4 days the presence of residual toxin in natural ponds rich in organic material was nil, whereas some distilled water test basins in the laboratory were unable to support mosquitos due to residual toxin for up to 13 months. These differences seem to reflect the high content of active proteases in organic rich pools which can inactivate the toxin. For some species such as Culex repeated application in field application may be necessary, while for others with a limited life cycle such as Anaopheles one application during the larval development period should be most effective.

I claim:

1. A biologically pure mutant of *Bacillus cereus* subspecies *israelensis* which is substantially non-spore-forming and which is selected from the group consisting of mutants bearing deposit numbers 1178, 1179 and 1180 with the culture collection of the University of Western Ontario, London, Ontario, Canada.

2. A biologically pure Spo III mutant of *Bacillus cereus* subspecies *israelensis* which is substantially non-spore-forming while being capable of forming inclusion bodies toxic to insects of the order Diptera in the larval stage, said mutant bearing deposit number 1178 with the culture collection of the University of Western Ontario, London, Ontario, Canada.

3. A biologically pure Spo II mutant of *Bacillus cereus* subspecies *israelensis* which is substantially non-spore-forming while being capable of forming inclusion bodies toxic to insects of the order Diptera in the larval stage, said mutant bearing deposit number 1179 with the culture collection of the University of Western Ontario, London, Ontario, Canada.

4. A biologically pure Spo II mutant of *Bacillus cereus* subspecies *israelensis* which is substantially non-spore-forming while being capable of forming inclusion bodies toxic to insects of the order Diptera in the larval stage, said mutant bearing deposit number 1180 with the culture collection of the University of Western Ontario, London, Ontario, Canada, and deposit number ATCC 39,152 with the American Type Culture Collection, Rockville, Md., U.S.A.

5. A method for producing a substantially spore-free insecticide active against insects of the order Diptera in the larval stage comprising growing a biologically pure non-spore-forming mutant of *Bacillus cereus* subspecies *israelensis* in a culture medium to the stage of formation of toxic inclusion bodies and lysis of the cells, and separating the toxic inclusion bodies from the culture medium, said mutant being selected from the group of mutants bearing deposit numbers 1178, 1179 and 1180 with the culture collection of the University of Western Ontario, London, Ontario, Canada.

6. A method as in claim 5 wherein the mutant bears deposit number 1180 with the culture collection of the University of Western Ontario, London, Ontario, Canada, and deposit number ATCC 39,152 with the American Type Culture Collection, Rockville, Md., U.S.A.

7. A method for producing a substantially spore-free insecticide active against insects of the order Diptera in the larval stage comprising growing a biologically pure non-spore-forming mutant of *Bacillus cereus* subspecies *israelensis* in a culture medium to the stage of formation of toxic inclusion bodies and lysis of the cells, separating fermentation products from the culture medium and subjecting the separated fermentation products to high shearing stress to liberate the toxic inclusion bodies, said mutant being selected from the group of mutants bearing deposit numbers 1178 and 1179 with the culture collection of the University of Western Ontario, London, Ontario, Canada.

8. A method as in claim 7 wherein said mutant bears deposit number 1178 with the culture collection of the University of Western Ontario, London, Ontario, Canada.

9. A method as in claim 7 wherein said mutant bears deposit number 1179 with the culture collection of the University of Western Ontario, London, Ontario, Canada.

10. A method as in claim 5 or 6, wherein the toxic inclusion bodies are separated from the culture medium by centrifugation.

11. A freeze-dried culture of the mutant of claim 2.

12. A freeze-dried culture of the mutant of claim 3.

13. A freeze-dried culture of the mutant of claim 4.

14. An insecticide active against insects of the order Diptera in the larval stage comprising as an active ingredient an effective larva killing concentration of substantially spore-free toxic inclusion bodies prepared by growing a biologically pure non-spore-forming mutant of *Bacillus cereus* subspecies *israelensis* in a culture medium to the stage of formation of toxic inclusion bodies and lysis of the cells, and separating the toxic inclusion bodies from the culture medium, said mutant being selected from the group of mutants bearing deposit numbers 1178, 1179 and 1180 with the culture collection of the University of Western Ontario, London, Ontario, Canada.

15. An insecticide active against insects of the order Diptera in the larval stage comprising as an active ingredient an effective larva killing concentration of substantially spore-free toxic inclusion bodies prepared by growing a biologically pure non-spore-forming mutant of *Bacillus cereus* subspecies *israelensis* in a culture medium to the stage of formation of toxic inclusion bodies and lysis of the cells, separating fermentation products from the culture medium and subjecting the separated fermentation products to high shearing stress to liberate the toxic inclusion bodies, said mutant being selected from the group of mutants bearing deposit number 1178 and 1179 with the culture collection of the University of Western Ontario, London, Ontario, Canada.

16. An insecticide as in claim 14 of 15 further comprising a carrier.

17. A method of controlling insects of the order Diptera in the larval stage comprising applying to larval habitats an effective concentration of substantially spore-free toxic inclusion bodies, prepared by growing a biologically pure non-spore-forming mutant of *Bacillus cereus* subspecies *israelensis* in a culture medium to the stage of formation of toxic inclusion bodies and lysis of the cells, and separating the toxic inclusion bodies from the culture medium, said mutant being selected from the group of mutants bearing deposit number 1178, 1179 and 1180 with the culture collection of the University of Western Ontario, London, Ontario, Canada.

18. A method of controlling insects or the order Diptera in the larval stage comprising applying to larval habitats an effective concentration of substantially spore-free toxic inclusion bodies, prepared by growing a biologically pure non-spore-forming mutant of *Bacillus cereus* subspecies *israelensis* in a culture medium to stage of formation of toxic inclusion bodies and lysis of the cells, separating fermentation products from the culture medium and subjecting separated fermentation products to high shearing stress to liberate the toxic inclusion bodies, said mutant being selected from the group of mutants bearing deposit numbers 1178 and 1179 with the culture collection of the University of Western Ontario, London, Ontario, Canada.

19. A method as in claim 17 or 18 wherein the concentration is at least $10^4$ inclusion bodies/ml. in the treated larval habitats.

* * * * *